United States Patent [19]

Etem

[11] Patent Number: 4,936,767
[45] Date of Patent: Jun. 26, 1990

[54] ROTATIONAL MOLDING OF ORTHODONTIC RETAINER

[76] Inventor: Robert R. Etem, 2705 Willow Dr., Long Lake, Minn. 55356

[21] Appl. No.: 352,155

[22] Filed: May 15, 1989

[51] Int. Cl.⁵ .................. B29C 41/04; B29C 41/12
[52] U.S. Cl. .................................. 425/434; 425/435; 425/457
[58] Field of Search ............... 425/435, 457, 425, 434; 264/16, 18

[56] References Cited

U.S. PATENT DOCUMENTS

| | | | |
|---|---|---|---|
| 3,909,179 | 9/1975 | Chujoo et al. | 425/429 |
| 4,104,357 | 8/1978 | Blair | 264/255 |
| 4,146,565 | 3/1979 | Quraishi | 264/310 |
| 4,183,883 | 1/1980 | Blair | 264/401 |
| 4,185,067 | 1/1980 | MacAdams et al. | 264/310 |
| 4,378,929 | 4/1983 | Huffman | 249/124 |
| 4,481,162 | 11/1984 | Huffman | 264/334 |
| 4,494,934 | 1/1985 | Huffman | 433/213 |
| 4,656,067 | 4/1987 | Yetter | 428/35 |
| 4,695,244 | 9/1987 | Friesen | 425/429 |

Primary Examiner—Willard Hoag
Attorney, Agent, or Firm—Faegre & Benson

[57] ABSTRACT

A device for forming an orthodontic retainer by rotational molding. The device facilitates the production of orthodontic bite retainer appliances by providing uniform mixing of the retainer liquid/powder precursors during the period of initial setting-up to assure a smooth, uniform product. Also described is a modification for providing more than one retainer at a time, as well as a modification to provide formation of the retainer under evacuated exhaust.

9 Claims, 2 Drawing Sheets

ROTATIONAL MOLDING OF ORTHODONTIC RETAINER

FIELD OF THE INVENTION

This invention relates to an apparatus and method for forming an orthodontic retainer by rotational molding. The apparatus of this invention is intended to facilitate the production of orthodontic bite retainer appliances by providing uniform mixing of the retainer liquid precursors during the period of setting-up to assure a smooth, uniform product.

BACKGROUND OF THE INVENTION

In order for an orthodontist to make an orthodontic retainer appliance, a mold must be made which is an exact impression of the individual patient's teeth and plate structure. Generally, a mixture of gelatin and plaster of paris is used which is in a fairly springy rubber-like configuration. This impression is then allowed to harden. This mold is then filled with an artificial stone and allowed to set up. This liquid material is generally a mixture of a monomer and polymer which must be evenly blended before and during the setting up period to assure a smooth, uniform and bubble-free product.

Previously, the typical process has been for the orthodontist or technician to manually rock the model and components back and forth gently during the setting up period, to assure an even distribution across the surface of the model, so that a fairly uniform thickness is obtained as the retainer sets. Approximately 5 to 10 minutes is required for the completion of the setting-up process by this manual procedure and it is usually only possible to prepare one retainer at a time. Following initial set, the model with the plastic resin is placed in a warm water bath and put under approximately 30 lbs. pressure.

SUMMARY OF THE INVENTION

According to the present invention, a device for rotational molding of an orthodontic retainer comprises:
a mounting plate supported on a motor shaft for axial rotation thereby at an oblique angle to the motor shaft axis of rotation;
means for mounting an orthodontic retainer mold on said mounting plate for rotation thereby;
such that, when the model is covered with liquid synthetic resin forming material and mounted on said mounting plate, rotation thereby assures even distribution of resin forming material in the orthodontic retainer.

A method for rotationally molding an orthodontic retainer according to the present invention comprises:
mounting an orthodontic retainer model layered with liquid synthetic resin forming material on a mounting plate, said mounting plate supported on a motor shaft for axial rotation thereby at an angle oblique to the motor shaft axis of rotation;
rotating the mounting plate and attached model during setting up of the liquid synthetic resin forming material to assure even distribution thereof in the orthodontic retainer.

These and other features of this invention will become obvious from the following drawings and detailed description of the preferred embodiment.

DETAILED DESCRIPTION OF THE INVENTION

Figure 1:
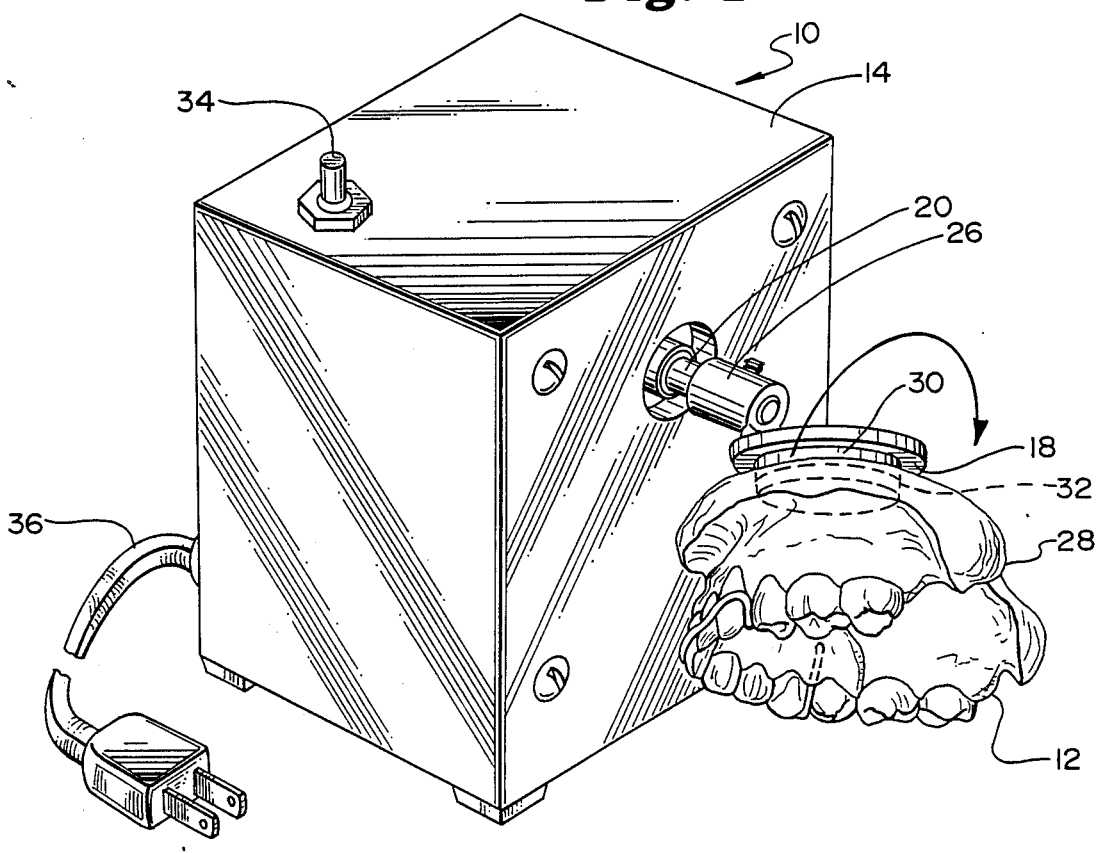
FIG. 1 is a perspective view of the preferred form of the invention along with an orthodontic retainer workpiece and an arrow showing axial rotation.
Figure 2:
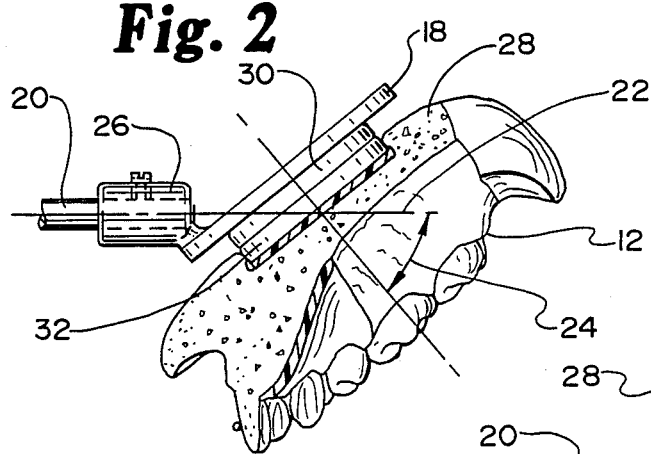
FIG. 2 is a fragmentary detail view orthographic to the axis of rotation and having parts broken away.
Figure 3:
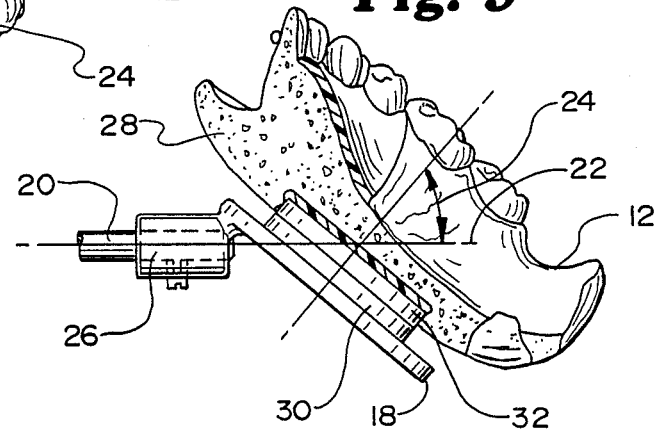
FIG. 3 is a view similar to that of FIG. 2, showing the axis rotated 180 degrees.
Figure 4:
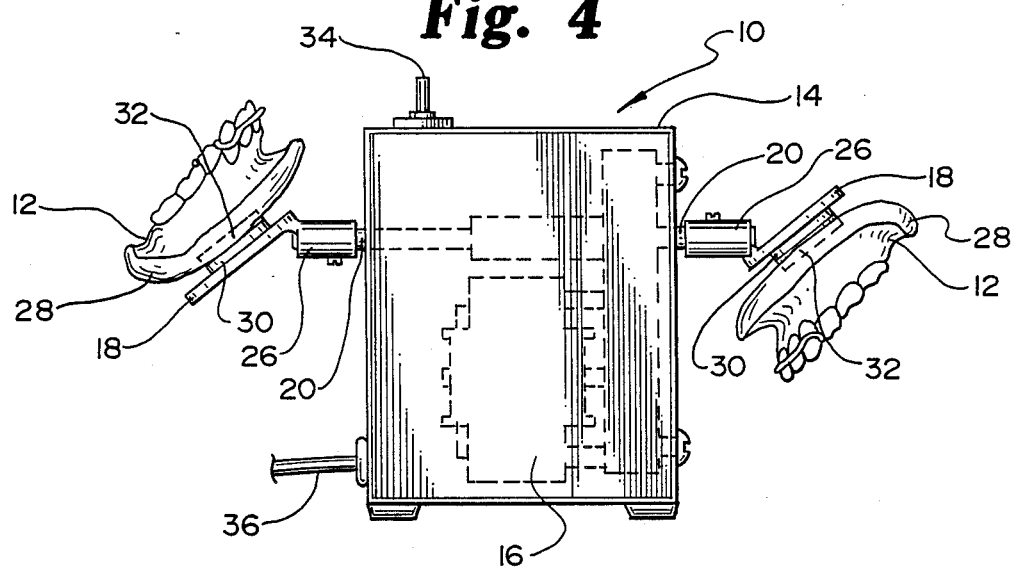
FIG. 4 is a front elevational view of an alternate form of the invention having more than one rotational mount.
Figure 5:
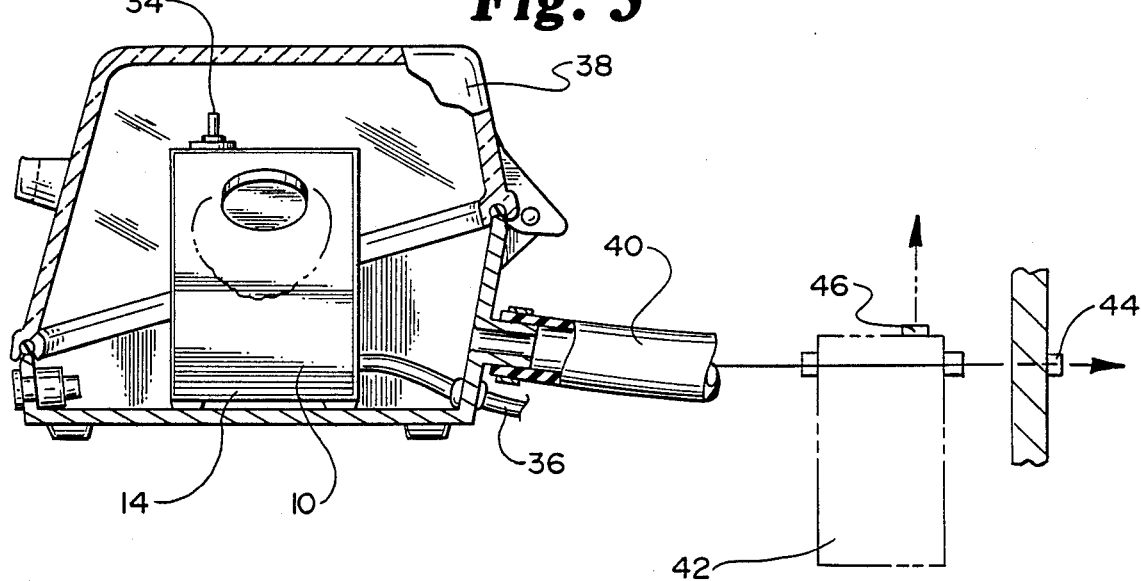
FIG. 5 is a side elevational view with parts cut away, of the invention enclosed within a sealed chamber having an evacuation system connected thereto.

A device 10 for rotational molding of an orthodontic retainer 12 according to the present invention is illustrated in FIG. 1. The enclosure 14 as illustrated in FIG. 1, 4 and 5 houses a gear motor 16. A suitable gear motor for the purposes of the present invention has been found to be DAYTON shaded pole gear motor, model no. 3M096, although any similar motor may be used. A mounting plate 18 is supported on the motor shaft 20 in a position to allow rotation of the mounting plate 18 by the motor shaft 20 at an angle 24 to the motor shaft axis of rotation 22 of any positive angle between 0–180 degrees. Preferably the mounting plate 18 had a sleeve 26 for attachment to the motor shaft 20 to maintain the mounting plate 18 at the preferred angle of 40–50 degrees. The face of the mounting plate 18 is provided with means for mounting an orthodontic retainer mold 28, such as a ceramic magnet 30.

As has been described previously, the mold for an orthodontic retainer appliance 28 must be an exact impression of the individual patient's teeth and plate structure. The method of making such a mold and the materials used therein are of course well known to those skilled in orthodontia. In order for the model 28 to be used with the device 10 of the present invention, a means for mounting the model 28 to the mounting plate 18 must be embedded in the back thereof, suitably a ceramic magnet 32 for mating to the mounting plate magnet 30. Once the model has been formed and filled with suitable liquid synthetic resin forming material, the model 28 is attached to the mounting plate 18, and the mounting plate sleeve 26 is attached to the motor shaft 20. The device is then activated, desirably by switch 34 providing power through the electrical power supply 36. Rotation of the model 28 during setting up of the liquid synthetic resin forming material assures even distribution of the resin forming material in the orthodontic retainer 12. Rotation of approximately 7 rpm has been found to be suitable, although speeds slightly slower or faster may be used if desired. The motor 16 may suitably provide uniform unidirectional rotation, or may be modified to provide oscillatory motion, or may also be provided with suitably camming to provide a period of unidirectional rotation, followed by reversal to an opposite direction of rotation.

As shown in FIG. 4, the device 10 of this invention may also provide for two or more mounting plates 18 to be supported by the motor shaft 20 for simultaneous rotation thereby.

Operation of the device of the present invention at ambient conditions of temperature and pressure has been found to give satisfactory results. Alternatively, FIG. 5 shows a side elevational view with parts cuts away, of a device 10 of the present invention enclosed within a vapor sealed chamber 38 having an evacuation system connected thereto. This evacuation system is used to evacuate residual gases from the synthetic resin during the initial setting-up process. The entire device, as shown in FIG. 1 or 4 is enclosed in the vapor sealed chamber 38 from which residual gases are extracted through exhaust line 40 by evacuation pump 42 to exhaust vent 44 or alternative clean filtered exhaust 46.

I claim:

1. A device for rotational molding of an orthodontic retainer comprising:

a mounting plate supported on a motor shaft for axial rotation thereby at an oblique angle to the motor shaft axis of rotation;

means for mounting an orthodontic retainer model on said mounting plate for rotation thereby;

such that, when the model is layered with liquid synthetic resin forming material and mounted on said mounting plate, rotation thereby assures even distribution of resin forming material in the orthodontic retainer.

2. A device according to claim 1, wherein the motor shaft axis of rotation is horizontal and the mounting plate axis of rotation is at an angle of 40–50 degrees to the motor shaft axis of rotation.

3. A device according to claim 1, wherein the orthodontic retainer model is a replication of an individual patient s teeth and plate structure.

4. A device according to claim 1, wherein the means for mounting the orthodontic model to the mounting plate comprises a magnet on the mounting plate mated to a magnet embedded in the orthodontic retainer model.

5. A device according to claim 1, wherein the device is rotatable with a uniform unidirectional rotation.

6. A device according to claim 1, wherein the device is rotatable with a an oscillatory motion.

7. A device according to claim 1, wherein the device has means for providing a period of unidirectional rotation, followed by reversal to an opposite direction of rotation.

8. A device according to claim 1, having a plurality of said means for mounting plates supported by the motor shaft for simultaneous rotation thereby.

9. A device according to claim 1, wherein the motor shaft axis of rotation is horizontal and the mounting plate axis of rotation is a 45 degree angle to the motor shaft axis of rotation.

* * * * *

UNITED STATES PATENT AND TRADEMARK OFFICE
CERTIFICATE OF CORRECTION

PATENT NO. : 4,936,767

DATED : June 26, 1990

INVENTOR(S) : Robert R. Etem

It is certified that error appears in the above-identified patent and that said Letters Patent is hereby corrected as shown below:

Column 4, line 5, claim 3, after "patient" insert --'--

Column 4, line 12, claim 5, delete "with a" and insert --in--

Column 4, line 14, claim 6, delete "with a" and insert --in--

Signed and Sealed this

Twenty-eighth Day of January, 1992

Attest:

HARRY F. MANBECK, JR.

*Attesting Officer*     *Commissioner of Patents and Trademarks*